United States Patent [19]

Calam et al.

[11] Patent Number: 5,057,497
[45] Date of Patent: Oct. 15, 1991

[54] ORAL METHOD FOR THE MAINTENANCE OF HEALTHY GINGIVAL TISSUES USING TRF

[75] Inventors: Henry D. Calam, Peekskill, N.Y.; Hans A. Schaeffer, Linden, N.J.

[73] Assignee: Calam & Associates, Inc., Peekskill, N.Y.

[21] Appl. No.: 379,078

[22] Filed: Jul. 13, 1989

Related U.S. Application Data

[63] Continuation-in-part of Ser. No. 119,142, Nov. 10, 1987, abandoned, which is a continuation-in-part of Ser. No. 791,377, Oct. 25, 1985, abandoned.

[51] Int. Cl.$^5$ .............. A61K 7/16; A61K 35/54; A61K 37/22
[52] U.S. Cl. .................. 514/21; 514/12; 514/900; 514/901; 514/902; 514/946; 514/947; 514/969; 424/49; 424/50; 424/559; 424/562
[58] Field of Search ............ 424/50, 49, 450, 95, 424/97, 559, 562; 514/21, 12, 946, 947, 969, 900-902

[56] References Cited

U.S. PATENT DOCUMENTS

| | | | |
|---|---|---|---|
| 2,239,345 | 4/1941 | Sperti | 167/74 |
| 2,320,478 | 6/1943 | Sperti | 424/107 |
| 2,320,479 | 6/1943 | Sperti | 424/107 |
| 2,532,206 | 11/1950 | Taub | 514/969 |
| 3,678,154 | 7/1972 | Widder | 424/52 |
| 4,247,411 | 1/1981 | Vanlerberghe et al. | 252/316 |
| 4,508,703 | 4/1985 | Redziniak et al. | 424/38 |
| 4,575,457 | 3/1986 | Mazarin | 424/52 |
| 4,608,211 | 8/1986 | Handjani et al. | 222/94 |

FOREIGN PATENT DOCUMENTS 0043738A 1/1982 European Pat. Off. .
0152414 8/1985 Japan .

OTHER PUBLICATIONS

Abst. of JA 0152414, Aug. 1985 (Derwent Abst. No. C85-101452).
Abst. of Eur. Pat. No. 88046, Sep. 1983 (Derwent Abst. No. C83-087308).
Liposomes, ed. by Ostro, Marcel Dekker, Inc., N.Y., 1983, 291-294.
West, Textbook of Biochemistry, 4th ed., The MacMillan Co., N.Y., 1966, pp. 342-343.
Abstract, EP 43,738, Procter & Gamble Co., Jan. 12, 1982.
Ostro, Liposomes, Marcel Dekker, Inc., N.Y., p. 66, 1983.
White, Principles of Biochemistry, 4th ed., McGraw-Hill Book Company, N.Y., p. 75, 1968.
Cook et al., Proceeding of the Society for Exp. Biology and Medicine, vol. 53, pp. 222-225 (1943).
Kreke et al., The Journal of Biological Chemistry, vol. 160, No. 1, pp. 105-110 (Sep. 1945).
Goodson et al., Journal of Surgical Research, vol. 21, pp. 125-129 (1976).
Kaplan, J. Z., Archives of Surgery, vol. 119, pp. 1005-1008 (Sep. 1976).
Subramanyam et al., Digestive Diseases and Sciences, New Series, vol. 29, No. 9 (Sep., 1984).

Primary Examiner—F. T. Moezie
Attorney, Agent, or Firm—Abelman Frayne & Schwab

[57] ABSTRACT

Absorption of Tissue Respiration Factor (TRF) into the gingival tissues is materially enhanced when it is formulated as a non-astringent hydrophilic pharmaceutical composition containing penetration promoting substances which are both hydrophilic and lipophilic. Additionally, a highly efficient means for effecting absorption of TRF into the gingival tissues is to utilize liposomes as carriers for the TRF in a non-astringent pharmaceutical composition.

5 Claims, No Drawings

ORAL METHOD FOR THE MAINTENANCE OF HEALTHY GINGIVAL TISSUES USING TRF

CROSS REFERENCE TO RELATED APPLICATIONS

This application is a continuation-in-part of co-pending application Ser. No. 119,142, filed Nov. 10, 1987, which is a continuation-in-part of application Ser. No. 791,377, filed Oct. 25, 1985, both now abandoned.

BACKGROUND OF THE INVENTION

1. Field of the Invention

The present invention relates to a composition for use in the oral cavity for the maintenance of healthy teeth and gingival tissue and, more specifically, to a composition for the maintenance of oral health which also stimulates the respiration of gingival tissue and promotes cellular proliferation and growth.

2. Description of the Related Art

It is known that substances, or factors, which stimulate the respiratory function of tissue and promote cellular growth and proliferation are produced when living cellular matter is injured under very specific conditions. The cellular matter can be derived from rat, mouse or chick embryos, rat spleen or liver, various types of bacteria, etc. The most conveniently available source of this matter is live Brewer's yeast (Saccharomyces cerevisiae) which, under the proper process conditions, yields a derivative which is now widely used for the treatment of hemorrhoids. This derivative has been variously designated as Live Yeast Cell Derivative (LYCD), Skin Respiration Factor (SRF), or Tissue Respiration Factor (TRF). It has been shown that TRF contains nucleotides, nucleosides, including guanine and adenine, amino acids, especially alanine, arginine and tyrosine; mono-and disaccharides, and phosphorus containing compounds.

The mechanism of the action of TRF in its enhancement of tissue respiration appears to depend, in part, on the stimulation of the enzyme peroxydase (via the oxidation of pyrogallol to purpurogallin) and catalase (splitting of hydrogen peroxide). These enzymatic processes are involved in the respiratory process, in the cytochrome portion of the respiratory chain.

In addition, investigations by Goodson, et al., infra, have produced evidence that TRF stimulates the oxygen utilization of human fibroblasts. Studies with human skin specimens as well as rat epithelium have shown that TRF caused an increase in the amount of collagen synthesized by the fibroblasts. These findings serve to indicate that the increased oxygen consumption is linked to increased collagen synthesis by the cell.

Numerous articles have been published in the scientific and lay literature and several issued patents support the highly beneficial effects of TRF on wound healing, the treatment of burns and the amelioration of skin disorders. Some of the relevant patents and publications are:

Sperti, G., U.S. Pat. No. 2,239,345 granted Apr. 22, 1941;

Sperti, G., U.S. Pat. No. 2,320,478, granted June 1, 1943;

Sperti, G., U.S. Pat. No. 2,320,479, granted June 1, 1943;

Goldman, H. M. and Cohen, D. W.: Periodontal Therapy, 6th edition;

Goldberg, J. V. et al., Your mouth is your business: The dentist's guide to better health, The C. V. Mosby Co., 1980;

Walker, J. A. and Helling, D. K.: Oral Health Products in Handbook of Nonprescription Drugs, 7th edition, Appleton, Century-Crofts, 1980;

Goodson, W. et al.: J. Surgical Res., 21, 125–129 (1976), "Augmentation of some aspects of wound healing by a "Skin Respiratory Factor"

Kaplan, J. Z.: Acceleration of wound healing by a Live Yeast Cell Derivative, Archives of Surgery, September. 1984, 119, 1005–1008;

Cook, E. S.: Skin health and respiration, Part 1 (January. 1939) Part 2 (August. 1939) Chemical Products, Publisher: Science Service, London, U.K.

Kreke, C. W. and Suter, A.: Activity mechanism of Yeast Extracts in Stimulating Respiration, J. Bio. Chem., 160, No. 1, 105–111 (1945);

Cook, E. S. and Kreke, C. W.: Effects of yeast extracts and phenylmercuric nitrate on yeast respiration and growth, Proc. Soc. Exp. Biol. and Med., 53, 222–225 (1943); and Subramanyam, K. et al.: Effects of Preparation-H on wound healing in the rectum of man, J. Digest. Dis. and Sci., 129, 9, 829–32 (1984).

In addition, the American Home Products Corporation has sponsored a large number of clinical studies which have been submitted to the Food and Drug Administration in support of their hemorrhoidal product Preparation H which includes TRF as the active agent. These studies have become available to the public under the Freedom of Information Act.

In a 1986 patent to Mazarin, U.S. Pat. No. 4,575,457, a pharmaceutical composition which when employed as a dentifrice is said to provide an effective therapy for gingivitis, is disclosed which comprises skin respiratory factor (SRF), and bicarbonate, fluoride and zinc salts. Since zinc salts are well-known and widely-used as astringents, the employment of such salts, and other astringents, would serve to harden the protein present in the gingivae and thus prevent or severely retard the penetration and absorption of the SRF into the gingivae. Furthermore, zinc ions will tend to inactivate SRF by precipitation and denaturation of the SRF polypeptide. Thus, the benefits to be obtained by the use of SRF in the prevention or amelioration of periodontal disease would be entirely or substantially negated by following the teaching of the Mazarin patent. In addition, since zinc salts are usually acidic in nature, they would react with the bicarbonate in Mazarin's composition causing its immediate breakdown and evolution of carbon dioxide. Accordingly, Mazarin's composition is totally lacking in commercial feasibility.

SUMMARY OF THE INVENTION

It has now been determined that the absorption of TRF into the gingival issue is increased thus promoting cellular proliferation and growth when it is formulated as a non-astringent dentifrice composition which includes a penetration promoting substance which is both lipophilic and hydrophilic, in a suitable pharmaceutical vehicle.

While it is not known with certainty, it is postulated that the absorption of TRF by gingival tissue is facilitated by the fact that TRF has a high partition coefficient. Substances of this type can be more readily absorbed by both hydrophilic and lipophilic systems. Since the cell membranes in gingival tissue are semipermeable, a material, such as TRF, which can partition itself into both aqueous and lipid environments, is able to enter into the cell membranes comparatively easily since it can pass through the natural oil and water barrier inherent in the cell walls. When TRF is formulated with the penetration promoting substances of the present invention, which are also both hydrophilic and lipophilic, the rate of absorption into the gingival tissue is increased materially. Rapid absorption is especially important when dealing with a dentifrice product since its residence time in the oral cavity, i.e., the period of time when it is in contact with the gingivae and teeth, is relatively short-lived considering the usual oral care regimen followed by most people. Accordingly, the hydrophilic dentifrice composition of the present invention has been specifically designed to maximize the absorption or delivery of TRF into the gingivae in the shortest time frame, namely, by including certain hydrophilic/lipophilic penetration promoting substances, while eliminating from the formulation any materials which would inactivate the TRF by precipitation, denaturation or otherwise, or which would prevent or retard absorption, such as astringents, e.g., zinc ions. Various conventional mild dental cleansing agents, orally effective antimicrobial agents, etc. may also be included in the pharmaceutical composition of the present invention to carry out their usual functions.

The amount of TRF employed can vary from about 200 to about 10,000 respiration units per ounce, with a composition containing from about 200 to about 5000 units being preferred, and a composition including from about 2000 to about 2500 units per ounce being especially preferred.

The penetration promoting substance, which is both hydrophilic and lipophilic, is selected from the group consisting of lanolin including hydrous lanolin, and derivatives thereof, derivatives, fatty acid esters or fatty alcohol esters which contain a lipophilic chain of from about 8 to about 25 carbon atoms in one moiety of the ester (in either the fatty acid or fatty alcohol moiety) and a hydrophilic chain of from about 1 to about 5 carbon atoms in the other moiety of the ester and ethoxylated higher (from about 8 to about 25 carbon atoms) fatty acid esters of polyhydric alcohols, and mixtures thereof.

Exemplary of the hydrophilic/lipophilic penetration promoting substances of the present invention, but not limited thereto, are: straight chain fatty alcohol esters, such as, propyl myristate; medium chain length fatty alcohol esters, such as, $C_{12}$-$C_{15}$ alcohols benzoate; branched chain fatty alcohol esters, such as, isopropyl myristate; partial fatty acid esters of polyhdric alcohols and their ethoxylated derivatives, such as, ethoxylated sorbitan monolaurate and capric/caprylic monodiglyceride; lanolin and its derivatives, such as, acetylated lanolin, lanolin alcohols, ethoxylated lanolin, propoxylated lanolin, as well as mixtures of the foregoing penetrant substances. The concentration of the penetration promoting substances in the pharmaceutical composition of the present invention can be from about 0.5% to about 10.0%, by weight.

The Tissue Respiration Factor and the penetration promoting substances are then formulated, for example, into a suitable gel, cream, or paste which are the preferred vehicles for application to the gingival tissue. Alternatively, a lotion or liquid may be employed since they assure a comparatively longer residence time on the gingivae.

The absorption of the TRF product can be enhanced by the user thoroughly rubbing the product into the gingival tissues. The rubbing or massaging can be readily carried out by applying it with the tip of one's finger or a suitable applicator.

Under these conditions the TRF enters the gingival structures and exerts its beneficial affects for a period greater than 24 hours. To achieve the best results, the procedure should be used in the morning and evening.

Additionally, it has now been found, in accordance with yet another embodiment of the present invention, that a highly efficient method for promoting the absorption of TRF and its incorporation into gingival tissue can be achieved by employing liposomes as carriers for the TRF in a pharmaceutical composition.

Liposomes are microscopic sacs or vesicles whose cell walls consist of phospholipids. All cell membranes in the mammalian body are made of phospholipids, hence these substances by-and-large are non-toxic and non-irritating. The vesicles are essentially cavities surrounded by multiple layers of phospholipids. Both water-soluble and oil-soluble drugs or other materials can be incorporated in these vesicles which due to their microscopic size (10 to 100 nanometers), as well as their physicochemical properties, easily penetrate epidermal structures, reaching the underlying tissues where the contents are released.

The characterization and preparation of liposomes has been thoroughly discussed in the scientific and patent literature, exemplary of which are:

M. J. Ostro: Liposomes. Marcel Dekker, Inc. New York, 1983

G. Gregoriades (ed.): Liposome Technology. CRC Press, 1984

M. J. Ostro: Liposomes, Scientific American, 256, No. Jan. 1, 1987

Vanlerberghe et al.: U.S. Pat. No. 4,247,411, Jan. 27, 1981

Rediziniak et al.: U.S. Pat. No. 4,508,703, Apr. 2, 1985

Handjani et al.: U.S. Pat. No. 4,608,211, Aug. 26, 1986

While these and other references disclose the chemistry, preparation and some applications of liposomes as carriers of a number of drug substances, none teaches the incorporation of Tissue Respiration Factor, nor the specific application of TRF-liposome to the oral cavity for the maintenance of healthy gingival tissues.

Because of the nature of the TRF-liposome it can be applied directly to the gingival tissues without the need of a pharmaceutical vehicle. For ease of handling, however, it is preferred that the TRF-liposome be formulated into any suitable pharmaceutical vehicle, such as in the form of a cream, paste, gel or lotion and thus could be applied as a dentifrice composition. The TRF-liposome dentifrice formulation should have eliminated therefrom any astringents or any materials which would inactivate the TRF polypeptide by precipitation, denaturation, or otherwise.

The activity of TRF can be assayed by measuring the increment of oxygen consumption of abdominal rat tissues upon exposure to TRF, as determined by means of the Warburg apparatus. A standard respiration unit (RU) is defined as the quantity of TRF which increases the oxygen consumption of 1 mg of rat abdominal tissue by 1% in a one hour period when measured by Warburg manometry. Viable TRF generally displays a potency of 7-12 RU per milligram. A method of preparation of Live Yeast Cell Extracts and similar cell stimulants has been disclosed in Sperti, U.S. Pat. No. 2,239,345, issued Apr. 22, 1941. This includes the TRF of the present invention. Topical remedies which embody this material for the treatment of cuts, burns, sores, skin eruptions and disorders are described in Sperti, U.S. Pat. No. 2,320,479, issued June 1, 1943.

Epithelization and collagen synthesis play an important role in the wound healing process. Similarly, during incipient and progressive periodontal disease, the gingival tissues are attacked and injured. Inflammation results, oxygen uptake is inhibited due to bacterial overgrowth, and the connective tissue which holds the teeth in place is gradually destroyed. Swollen, bleeding gums may result due to reduction in (or poorly formed) collagen which can lead to the eventual loosening and loss of teeth. Intricately involved in this disease process is the degradation and final destruction of the connective tissue fibers and ligaments which form the bond between alveolar bone and the cementum that surrounds the roots.

A dental product containing the collagen-building substances in TRF, the penetration promoting substances of the present invention, preferably with mild dental cleansing agents and effective and specially formulated antimicrobial compounds, when combined with a brushing regimen and use of a rubber-tip stimulator/applicator will be highly efficacious in the inhibition of his disease process which affects over 90% of all adults.

The TRF dental product of the present invention is specifically formulated to penetrate and be rapidly absorbed into interdental spaces, specifically the indentation between teeth and gingiva (sulcus) where the primary attack on the tissue fibers, ligaments and mucosa takes place. The product is preferably used in a two-step daily regimen as follows:

1. Cover the brush tips with the dental product of the present invention and thoroughly brush the teeth. Brush back and forth with short gentle strokes keeping the brush angled toward the gums. Brush at a 45° angle rotating gently in place and brushing upwards. Rinse thoroughly to remove all debris. (It is recommended to use a brush recognized as safe and effective by the American Dental Association (ADA) council on Dental Materials, Instruments and Equipment. Such a brush would have long, soft bristles for cleaning along the gumline and easy and gentle penetration into the sulcus to remove debris).

2. Once the brushing, cleaning and rinsing process is complete, apply a small amount of product directly in the gingival margins. Massage gently but thoroughly into these surfaces and into the sulcus using a finger or applicator. A rubber-tip stimulator/applicator is recommended for most effectively massaging into the crevices between the gums and teeth.

This procedure and similar modes of application will result in effective cleansing and removal of debris and dental plaque. It will help open the sulcus for cleansing purposes and for better infiltration and absorption of the active TRF substances into the gingival structures. In addition, it will effectively reduce the bacterial population on teeth and gums and thereby help to prevent the build-up of plaque as well as combat infections by pathogens.

Oral products of the present invention can be formulated in a number of forms, such as gels, pastes or creams as are set forth in the examples which follow.

EXAMPLE 1

Gel (Without Penetration Promoting Substance)

Clear, aesthetically appealing gels are formulated in the following manner.

Humectants are used in dentifrices to promote mixing with the saliva in the mouth. Commonly used humectants are glycerin, 70% sorbitol, propyleneglycol, polyethylene glycol and mixtures thereof. They are combined with bodying agents which provide high viscosity, such as, carboxymethyl cellulose, hydroxyethyl cellulose, hydroxypropyl cellulose or other cellulose gums, alginates or natural gums or mixtures thereof. When the gum is properly dispersed, an aqueous solution of sweetner, preservative and TRF is added. To the resulting vehicle is added a blend of mildly abrasive and thickening silicas which have the same refractive index as the vehicle, thus producing a clear substance.

To the gel, which has been deaerated in a vacuum vessel, is then added a moderate amount of anionic foaming agent, such as, sodium lauryl sulfate, sodium N-lauroyl sarcosinate, sodium coconut monoglyceride sulfonate, sodium N-methyl-N-palmitoyl lauride, or a water soluble salt of an olefin sulfonate, or nonionic surfactants such as polysorbates or poloxamers, followed by colors and flavors. A toothpaste must be deaerated to avoid any disruption of its homogeneity.

Finally, under moderate agitation, a warm, oleaginous dispersion of a finely divided antimicrobial substance such as, but not limited to, bezalkonium chloride, benzethonium chloride, cetylpyridinium chloride, povidone-iodine, chlorhexidine gluconate, hydroxyquinoline sulfate, hexylresorcinol, or neomycin sulfate is slowly added, forming distinctive and well-defined droplets in the gel.

The resulting gel has a low abrasivity index determined by the Radioactive Dentin Analysis (RDA) assay, i.e., 120 or less (CMC control: 18, calcium pyrophosphate reference standard: 475). The viscosity is suitable for the product to form a ribbon when squeezed out of a tube, and said ribbon will hold its shape on the toothbrush. At the same time, the consistency is soft enough that the product can be readily applied to and spread on teeth and gums.

Concentration ranges of the constituents are:

| Humectants | 10–70% |
| --- | --- |
| Bodying agents | 0.1–2.0% |
| TRF | 200–10,000 RU per ounce |
| Preservatives | 0.05–0.5% |
| Silicas | 2.0–40% |
| Foaming agents | 0.1–6% |
| Colors | 0.01–0.5% |
| Sweeteners & flavors | 0.1–2.5% |
| Oleaginous vehicle | 0.0–3.5% |
| Antimicrobial agent | 0.0–1.5% |

A specific gel composition is:

| Glycerin | 20.0% |
| --- | --- |
| Sorbitol 70% | 40.0 |
| Sodium Carboxymethyl cellulose | 0.3 |
| Sodium saccharin | 0.2 |
| Sodium benzoate | 0.2 |
| Silica blend | 18.5 |
| Sodium lauryl sulfate | 1.0 |
| Color, flavor | q.s |
| Purified water | q.s |
| TRF | 2000 RU per ounce |

-continued

| | |
|---|---|
| Petrolatum with 5% polyethylene (mol. wt. 21,000) | 1.5 |
| Cetyl pyridinium chloride | 0.05 |

EXAMPLE 2

Gel (With penetration promoting substance)

Listed below is a gel dentifrice formulation which includes a penetration promoting substance in accordance with the present invention and which was prepared in accordance with the procedure set forth in Example 1, supra.

Concentration ranges of the constituents are:

| | |
|---|---|
| Humectants | 10–70% |
| Bodying agents | 0.1–2.0% |
| Penetration promoting substance | 0.5–10.0% |
| TRF | 200–10,000 RU per ounce |
| Preservatives | 0.05–0.5% |
| Silicas | 2.0–40.0% |
| Foaming agents | 0.1–6.0% |
| Colors | 0.01–0.5% |
| Sweeteners & Flavors | 0.1–2.5% |
| Oleaginous vehicle | 0.0–3.5% |
| Antimicrobial agent | 0.0–1.5% |

A preferred gel composition in accordance with the present invention is as follows:

| | |
|---|---|
| Glycerin | 20.0% |
| Sorbitol 70% | 40.0 |
| $C_{12}$–$C_{15}$ alcohols benzoate (Finsolv TN) | 5.0 |
| Sodium carboxy methyl cellulose | 0.3 |
| Sodium saccharin | 0.2 |
| Sodium benzoate | 0.2 |
| Silica blend | 18.5 |
| Sodium lauryl sulfate | 1.0 |
| Color, flavor | q.s. |
| Purified water | q.s. |
| TRF | 2,000 RU per ounce |
| Petrolatum with 5% polyethylene (m.w. 21,000) | 1.5 |
| Cetyl pyridinium chloride | 0.05 |

The resulting gel is found to be an extremely effective therapy for gingivitis since the rate and degree of absorption of TRF is substantially increased relative to the gel of Example 1, thus promoting increased cellular proliferation and growth.

EXAMPLE 3

Paste

A paste in accordance with the present invention is prepared in the following manner.

Humectants which are commonly used in dentifrices, such as, glycerin, sorbitol 70%, propyleneglycol, polyethylene glycol and/or combinations thereof are combined with bodying agents such as sodium carboxymethyl cellulose, hydroxyethyl cellulose, methyl cellulose, hydroxypropyl methylcellulose and other cellulose gums, alginates or other natural gums such as xanthan, karaya, etc.

Once the gum is properly dispersed, a solution of preservatives, such as, methyl and propyl parabens, sodium benzoate or potassium sorbate, sodium saccharin and TRF is added, followed by the addition of a stabilizer, such as, magnesium aluminum silicate.

To the homogeneous dispersion are added cleansing and polishing agents such as dicalcium phosphate dihydrate, dicalcium phosphate anhydrous, hydrated aluminum oxide, calcium carbonate, calcium sulfate, silicates, sodium bicarbonate, or other commonly used abradents/polishing agents, or mixtures thereof.

Upon thorough agitation and degassing in a vacuum vessel, a foaming agent such as sodium lauryl sulfate, sodium N-lauroyl sarcosinate, sodium coconut monoglyceride sulfonate. or other suitable agent is added, followed by flavors and colors.

Finally, under moderate agitation, a warm, oleaginous dispersion of finely divided antimicrobial substances, such as, but not limited to, benzalkonium chloride, benzethonium chloride, cetylpyridinium chloride, povidone-iodine, chlorhexidine gluconate, hydroxyquinoline sulfate, hexylresorcinol, or neomycin sulfate is slowly added, forming distinctive and well defined droplets in the paste. The oleaginous carrier can consist of petrolatum, or high viscosity mineral oil, with the addition of polyethylene of suitable molecular weight, say, between 20,000 and 30,000, with or without the addition of waxes.

The paste is passed through a mill and degassed.

Concentration ranges of the constituents are as follows:

| | |
|---|---|
| Humectants | 10–70% |
| Bodying agents | 0.1–5% |
| Penetration promoting agents | 0.5–10.0% |
| Preservatives | 0.05–0.5% |
| Cleansing and polishing agents | 5–60% |
| Foaming Agents | 0.1–6% |
| Colors, flavors, sweeteners | q.s. |
| Purified water | q.s. |
| TRF | 200–10,000 RU per ounce |
| Oleaginous vehicle | 0.0–3.5% |
| Antimicrobial agent: | 0.0–1.5% |

A preferred paste composition is as follows:

| | |
|---|---|
| Glycerin | 12.0% |
| Sorbitol 70% | 28.0 |
| $C_{12}$–$C_{15}$ alcohols benzoate | 5.0 |
| Sodium carboxymethyl cellulose | 2.2 |
| Methyl paraben | 0.15 |
| Propylparaben | 0.05 |
| Magnesium aluminum silicate | 1.0 |
| Dicalcium phosphate. 2H$_2$O | 42.0 |
| Color, flavors | q.s. |
| Purified Water | q.s. |
| TRF | 2,000 RU per ounce |
| Petrolatum with 5% polyethylene (m.w. 21,000) | 1.5 |
| Cetylpyridinium chloride | 0.05 |

The resulting paste has a suitable viscosity for ready application to the toothbrush and a relatively low abrasivity index when determined by the Radioactive Dentin Analysis.

EXAMPLE 4

Liquid

A dental liquid is compounded with identical materials as the paste, but using reduced concentrations of bodying and thickening agents, as well as lower concentrations of cleansing and polishing agents and with the addition of soluble and compatible antimicrobial agents.

EXAMPLE 5

Cream

Listed below is a composition containing Tissue Respiration Factor and a mixture of penetration-promoting substances which are formulated into a cream for application to gingival tissue.

| (A) | Cetyl alcohol, NF | 3.0% | |
| --- | --- | --- | --- |
| | Stearic acid, double pressed | 2.0 | |
| | $C_{12-15}$ alcohols benzoate | 5.0 | |
| | Acetylated lanolin | 2.0 | |
| | Sorbitan sesquioleate | 0.5 | |
| | Mineral Oil | 6.0 | |
| | Propyl paraben | 0.1 | |
| (B) | Demineralized water | 70.04 | |
| | Carbomer 940 (B. F. Goodrich) | 0.25 | |
| | Methyl paraben | 0.20 | |
| (C) | Glycerin | 3.0 | |
| | TRF (10 RU/mg) | 0.71 | (equivalent to 2000 RU/oz) |
| | Demin. water | 3.00 | |
| (D) | Demin. water | 3.0 | |
| | Potassium hydroxide pellets | 0.3 | |
| | Tetrasodium EDTA | 0.1 | |
| (E) | Sodium saccharin q.s | 0.2 | |
| | Mint Flavor q.s. | 0.6 | |
| | | 100.00 | |

The procedure for the preparation of the above composition in the form of a cream involved heating (A) to 75° C. and adding it to (B), while maintaining rapid agitation. Thereafter, the mixture of (A) and (B) was cooled to 40° C. while constantly agitating and simultaneously slowly adding (C) thereto. Agitation was then slowed and (D) was then added. Then (E) was added while thoroughly agitating the mixture and it was allowed to come to room temperature. Thereafter, the cream was filled into suitable containers.

The TRF-containing cream of this example prepared in accordance with the above procedure was tested in several subjects. The subjects rubbed the cream into their gingival tissue twice a day, morning and evening, for a period of one week. It resulted in firming of the gingival tissue, reduced or eliminated bleeding and imparted a distinct feeling of improvement to the gingival tissue of the upper and lower gums.

EXAMPLE 6

Preparation of a TRF-liposome 450 grams of soy lecithin and 50 grams of cholesterol is dispersed in 3 liters of chloroform. The dispersion is agitated at 50° C. for 1 hour. The solvent is then removed in a rotary vacuum still, yielding a free-flowing, white powder. Traces of adhering solvent are removed in a vacuum oven at 50° C.

The dry powder is dispersed in 3 liters of 0.9% sodium chloride solution containing 150 grams of TRF having a potency of 15 respiration units per mg. The dispersion is kept under rapid agitation by means of a Homomixer and passed through a high-pressure homogenizer, the Microfluidizer, made by the Microfluidics Corporation of Newton, M.A. The pump is adjusted to a flow rate of 85 ml/min. with an operating pressure of 8-9,000 p.s.i. The batch is recycled for 25 passes.

The resulting liquid (Yield: 2.9 liters) is practically clear showing a slight opalescence and containing spherical vesicles with an average diameter of 85 nm. On standing or centrifugation, no sedimentation takes place.

A respiration assay showed a potency of 738 units/ml, which is well within the calculated value of 750 u/ml and assay accuracy.

The liquid is immediately preserved using methyl-, propyl- and butyl parabens and propyleneglycol.

Volume of liquid required for 2,000 Units: 2.7 ml Concentration in finished product at 2,000 Units per oz: 9 ml/100 or 9.0% v/v.

Similar TRF liposomes can be prepared using phosphatidyl glycerol, egg phosphatidylcholine, sitosterol, bile acids, or sphyngomyelin to have similar physical characteristics.

EXAMPLE 7

The Formation of a Hydrophilic Cream Employing the TRF liposome of Example 6 and the Procedure for its Preparation A finished hydrophilic cream suitable for use in the oral cavity is prepared as follows:

| (A) | Cetyl alcohol | 4.1% | |
| --- | --- | --- | --- |
| | Glyceryl stearate | 1.8 | |
| | Mineral oil | 1.7 | |
| | Stearic acid, double pressed | 0.75 | |
| | PEG-40 sorbitan lanolate | 0.4 | |
| | Propylparaben | 0.05 | |
| (B) | Demineralized water | 78.95 | |
| | Triethanolamine (85%) | 0.70 | |
| | Methylparaben | 0.25 | |
| (C) | Sodium saccharin q.s. | 0.2 | |
| | Mint flavor q.s. | 0.6 | |
| (D) | Glycerin | 1.5 | |
| | TRF liposome (5.0% active) | 9.0 | (equivalent to 2000 RU/oz) |
| | | 100.00 | |

Procedure

Heat (A) to 70°-75° C. and add to (B) with rapid agitation. Maintain at this temperature with agitation for 1 hour. Under constant agitation, cool to 40° C., and add (C). Cool to room temperature and add (D).

The cream is then filled into suitable, specially steamed and washed containers, observing super-clean conditions.

All of the foregoing products can be formulated to contain an anti-caries agent, such as, sodium fluoride or other suitable fluorine containing substances, which are well-known to those skilled in the art.

In preparing the compositions of this invention, the TRF is added to the composition, and the composition thereafter maintained, at a temperature below about 48° C., preferably no more than about 40° C. since it has been found that when compositions containing the TRF are subjected to higher temperatures, the TRF is materially degraded, resulting in reduced activity and malodorous osmophore byproducts.

The products are filled in suitable containers, such as collapsible tubes (plastic or metal) for gels and pastes and plastic bottles for liquids. Also, pumps can be used for gels, pastes and liquids for the convenient dispensing of these products.

This invention has been described with respect to suitable embodiments of dentifrice ingredients and pharmaceutical compositions for maintenance of healthy gingival tissue. It will be understood that modifications and variations thereof obvious to those skilled in the art are to be included within the spirit and purview of this application and the scope of the appended claims.

What is claimed is:

1. A method of treating gingival tissue which comprises applying to the gingival tissue a non-astringent pharmaceutical composition which comprises from about 200 to about 10,000 units per ounce of Tissue Respiration Factor, and from about 0.5% to about 10% by weight, of a penetration promoting substance which is both lipophilic and hydrophilic in a suitable pharmaceutical vehicle whereby the amount and rate of absorption of the Tissue Respiration Factor by the gingival tissue is increased thus promoting cellular proliferation and growth, in the absence of zinc ions.

2. A method of treating gingival tissue in accordance with claim 1 wherein the penetration promoting substance, is lanolin, hydrous lanolin, fatty acid esters or fatty alcohol esters which contain a lipophilic chain of from about 8 to about 25 carbon atoms in one moiety of the ester in either the fatty acid or fatty alcohol moiety and a hydrophilic chain of from about 1 to about 5 carbon atoms in the other moiety of the ester, ethoxylated higher $C_8$-$C_{25}$ fatty acid esters of polyhydric alcohols, and mixtures thereof.

3. A method of treating gingival tissue in accordance with claim 2, wherein the penetration promoting substance is propyl myristate, isopropyl myristate, $C_{12}$-$C_{15}$ alcohols benzoate, ethoxylated sorbitan monolaurate, capric/caprylic monodiglyceride, lanolin alcohols, acetylated lanolin, ethoxylated lanolin, propoxylated lanolin, and mixtures thereof.

4. A method of treating gingival tissue in accordance with claim 3 wherein the penetration promoting substance is $C_{12}$-$C_{15}$ alcohols benzoate.

5. A method of treating gingival tissue in accordance with claim 1 wherein the concentration of Tissue Respiration Factor is from about 200 to about 5000 units per ounce.

* * * * *